(12) United States Patent
Shah

(10) Patent No.: US 6,585,936 B1
(45) Date of Patent: Jul. 1, 2003

(54) SLIDE STAINER WITH CONTROLLED FLUID FLOW

(75) Inventor: Preyas Sarabhai Shah, 591 10th Ave., Warminster, PA (US) 18974

(73) Assignee: Preyas Sarabhai Shah, Warminster, PA (US)

(*) Notice: Subject to any disclaimer, the term of this patent is extended or adjusted under 35 U.S.C. 154(b) by 0 days.

(21) Appl. No.: 10/184,443

(22) Filed: Jun. 28, 2002

(51) Int. Cl.[7] .............................. G01N 35/00; B05C 3/00
(52) U.S. Cl. ............................ 422/63; 422/65; 422/67; 422/104; 436/46; 436/47; 436/48; 118/625; 118/423; 118/425; 427/2.11
(58) Field of Search .............................. 422/63, 65, 67, 422/104; 436/46, 47, 48; 118/625, 423, 425; 427/2.11

(56) References Cited

U.S. PATENT DOCUMENTS

| | | | | |
|---|---|---|---|---|
| 3,650,437 A | * | 3/1972 | Binnings et al. ............. 222/136 |
| 3,836,335 A | | 9/1974 | Eppes ......................... 23/259 |
| 3,837,795 A | * | 9/1974 | Becker et al. ............... 118/423 |
| 4,092,952 A | | 6/1978 | Wilkie et al. ................ 118/58 |
| 4,109,314 A | | 8/1978 | Meyer et al. ................. 364/552 |
| 4,200,607 A | | 4/1980 | Suzuki ........................ 422/64 |
| 4,436,764 A | * | 3/1984 | Nakazima et al. ........... 118/423 |
| 4,738,824 A | * | 4/1988 | Takeuchi ..................... 118/425 |
| 4,911,098 A | * | 3/1990 | Tabata ......................... 118/423 |
| 5,009,185 A | | 4/1991 | Stokes et al. ................. 118/52 |
| 5,180,606 A | | 1/1993 | Stokes et al. ................. 427/2 |
| 5,232,196 A | * | 8/1993 | Hutchings et al. ...... 251/129.08 |
| 5,273,905 A | | 12/1993 | Muller et al. ................ 435/301 |
| 5,354,370 A | * | 10/1994 | Schmehl ..................... 118/421 |
| 5,573,727 A | * | 11/1996 | Keefe .......................... 118/423 |
| 5,601,650 A | * | 2/1997 | Goldbecker et al. ......... 118/425 |
| 5,895,628 A | * | 4/1999 | Heid et al. ................... 118/423 |
| 5,895,762 A | * | 4/1999 | Greenfield et al. .......... 422/100 |
| 6,045,759 A | | 4/2000 | Ford et al. ................... 422/103 |
| 6,080,363 A | * | 6/2000 | Takahashi et al. ........... 118/625 |
| 6,093,574 A | | 7/2000 | Druyor-Sanchez et al. . 436/180 |
| 6,096,271 A | * | 8/2000 | Bogen et al. ................ 422/100 |
| 6,180,061 B1 | | 1/2001 | Bogen et al. ................. 422/64 |
| 6,183,693 B1 | | 2/2001 | Bogen et al. ................. 422/64 |
| 6,352,861 B1 | | 3/2002 | Copeland et al. ............ 436/46 |

* cited by examiner

*Primary Examiner*—Jill Warden
*Assistant Examiner*—Kathryn Bex
(74) *Attorney, Agent, or Firm*—RatnerPrestia

(57) ABSTRACT

An automated slide stainer with fluid flow control. The fluid flow control controls the flow rate of fluid, e.g., water, applied to at least one slide by the slide stainer. In an automated slide stainer that applies reagents to slides to stain biological specimens on the slides, the flow rate controlled fluid can be used to adequately rinse the slides without damaging the biological specimens contained on the slides.

6 Claims, 2 Drawing Sheets

SLIDE STAINER WITH CONTROLLED FLUID FLOW

FIELD OF THE INVENTION

The present invention relates to medical equipment and, more particularly, to methods and apparatus for staining specimens deposited on slides.

BACKGROUND OF THE INVENTION

Currently, many medical tests are performed by examining a biological specimen, e.g., blood, pus, or urine, applied to a slide, such as a conventional glass microscope slide. Typically, the biological specimen is "smeared" onto the slide and, then, treated with a reagent, such as a stain, to make features of the smeared biological specimen more visible. Often, the slide is then rinsed to remove excess reagent and dried for handling by laboratory personnel.

Automated slide stainers are available which automate the process of staining, rinsing, and drying smeared slides. One type of automated slide stainer is a dip and dunk slide stainer. In a dip and dunk slide stainer, one or more reagents are applied to slides by dipping the slides into one or more vessels containing these reagent. The slides are then rinsed by dipping the slides into a rinsing vessel, supplying water (or rinse solution) to the rinsing vessel, such that the water passes over the slides, and removing the slides from the rinsing vessel. Finally, the slides are dried by circulating air over them.

During the rinsing process, water supplied by a water supply line enters the rinsing vessel through an opening in the bottom of the rinsing vessel, thereby introducing water and causing the water within the rinsing vessel to circulate over the slides. Excess water, along with any reagents removed from the slide, exits the rinsing vessel through an opening near the top of the rinsing vessel. If the flow rate of the water into the rinsing vessel is too low, the slides will not be cleaned adequately, e.g., excess reagent will remain on the slides. On the other hand, if the flow rate is too high, the smeared biological specimen may be damaged or destroyed.

Typically, the flow of water is set using a manually operated valve. The valve is positioned in a rinse line between the water supply line and the opening in the bottom of the rinsing vessel. The valve is manually adjusted through trial and error to achieve an appropriate flow of water into the rinsing vessel. Thus, the appropriate flow is not precise and significant set-up time is required to achieve the appropriate flow. In addition, if the water pressure in the water supply line changes, e.g., due to a flushed toilet, an opened faucet, or other water supply line fluctuations, the flow of water changes, thereby increasing the potential for inadequately rinsed slides and/or damaged specimens.

Accordingly, there is a need for a slide stainer with controlled fluid flow for controlling the flow of rinse fluid supplied by a supply line to adequately rinse slides without damaging or destroying smeared biological specimens. The present invention fulfills this need among others.

SUMMARY OF THE INVENTION

The present invention is a slide stainer with controlled fluid flow. The slide stainer overcomes the aforementioned problems by controlling the flow rate of fluid, e.g., rinse fluid, from a fluid supply line that is applied to the slides. By controlling the flow rate of the fluid applied to the slides, a proper flow rate can be maintained regardless of the fluctuations in the flow in the supply line, thereby guarding against inadequately rinsed slides and/or damaged specimens.

In accordance with one aspect of the invention, fluid from a fluid supply line passes through a controlled flow device that can be controlled to regulate the flow rate of the fluid. The flow rate is sensed by a sensor, which produces a flow rate signal indicative of the sensed flow rate. Based on the flow rate signal, a controller generates a flow control signal for controlling the controlled flow device to control the flow rate of the fluid.

DETAILED DESCRIPTION OF THE INVENTION

Figure 1:
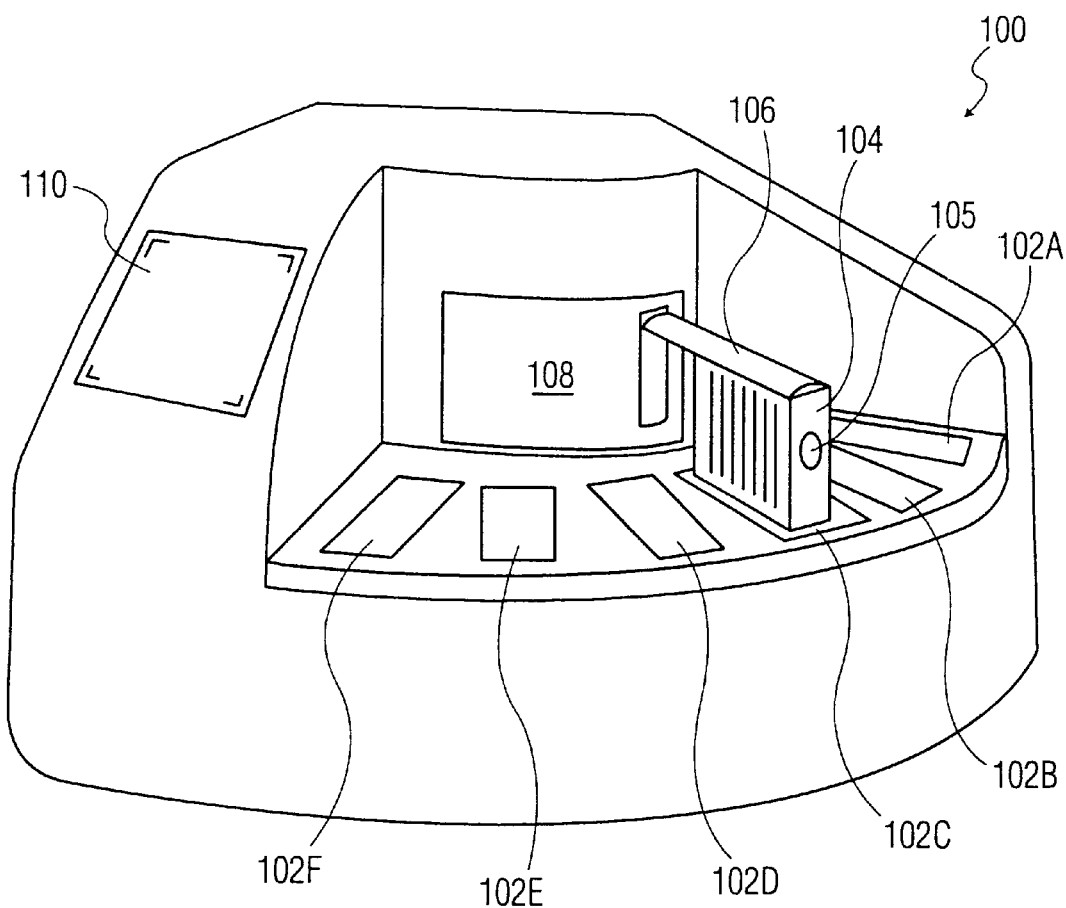
FIG. 1 is an illustration of a slide stainer in accordance with the present invention.

FIG. 1 depicts an automated slide stainer 100 for use in describing the present invention. The slide stainer 100 includes a plurality of cavities 102A–F, e.g., six in the illustrated embodiment, that are used to stain, rinse, and dry one or more slides 104 containing one or more specimens 105. For example, four of the cavities, e.g., 102A–D, may contain staining vessels filled with known reagents for staining the slides 104; one cavity, e.g., 102E, may contains a rinsing vessel for rinsing excess reagent from the slides 104 after staining; and one cavity, e.g., 102F, may contain known drying apparatus for drying the slides 104 after staining and rinsing. It will be recognized by those skilled in the art that the slide stainer 100 may contain essentially any number of cavities with some or all them being used for staining, rinsing, and/or drying.

The slides 104 are transported between the cavities 102A–F by a transport system that includes a transport arm 106 and transport mechanism 108. The transport arm 106 is configured to support the slides 104 in a known manner. The transport arm 106 is coupled to the transport mechanism 108, which is configured based on instructions received from a processor (not shown) to position the transport arm 106 in a known manner. The transport mechanism 108 may be configured to move the transport arm 106 in an arcuate pattern such that the transport arm 106 can be selectively positioned over each of the cavities 102E–F, and to lower and raise the transport arm 106 such that the slides 104 can be dipped into selected ones of the cavities 102A–F.

Using a key pad 110, an operator of the slide stainer 100 programs the processor to configure the transport mechanism 108 such that the slides 104 supported by the transport arm 106 are selectively positioned within the plurality of cavities 102A–F for a programmed amount of time in order to stain, rinse, and/or dry the slides 104. In addition, the processor may be programmed to agitate the slides 104 within one or more of the cavities 102A–F. Also, the processor may be programmed to control the flow of rinse fluid to the rinsing cavity 102E and to control the drying apparatus within the drying cavity 102F. Suitable transport system components, such as the transport arm 106, the transport mechanism 108, the processor, and the keypad 110, for use in the present invention will be readily apparent to those skilled in the art.

In use, the automated slide stainer 100 can be programmed by an operator to automatically perform a staining procedure to stain, rinse, and/or dry slides. For example, assume that a staining procedure requires that two reagents be applied to the slides 104, that the slides 104 be rinsed to remove excess reagent, and that the slides 104 be dried. Further, assume that a first reagent cavity, e.g., cavity 102A, and a second reagent cavity, e.g., cavity 102B, contain vessels filled with first and second reagents, respectively; that a rinsing cavity, e.g., cavity 102E, contains a rinsing vessel for rinsing the slides 104; and that a drying cavity, e.g., cavity 102F, contains drying apparatus for drying the slides 104. In this example, the processor is programmed via the keypad 110 to configure the transport mechanism 108 such that the control arm 106 sequentially positions the slides 104 within the first reagent cavity 102A for a first programmed amount of time, within the second reagent cavity 102B for a second programmed amount of time, within the rinsing cavity 102E for a third programmed amount of time to remove at least a portion of the first and second reagents, and within the drying cavity 102F for a fourth programmed amount of time. In addition, the processor is programmed to control the amount of time rinse fluid is supplied to the rinsing cavity 102E and the flow rate of the rinse fluid. The processor is also programed to control the drying apparatus within the drying cavity 102F.

It will be recognized by those skilled in the art that the slide stainer 100 can be programmed in an essentially infinite number of ways. For example, the slide stainer 100 can be programmed to dip the slides 104 into any one or more of the cavities 102A–F in any order. In addition, the amount of time the slides 104 are dipped into each cavity 102A–F and the amount of time between dips can be controlled. Rinse fluid and drying parameters can be controlled as well.

Figure 2:
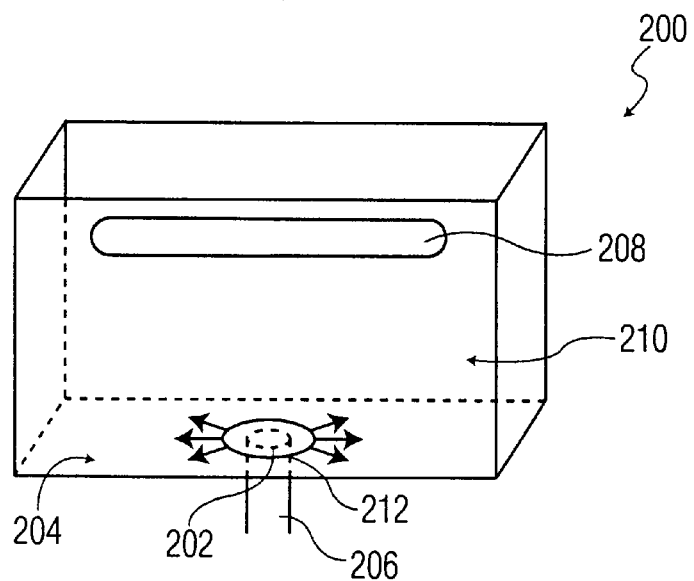
FIG. 2 is an illustration of a rinse vessel for use in the slide stainer of FIG. 1.

FIG. 2 depicts a preferred rinse vessel 200 that may be positioned within one of the cavities 102A–F (FIG. 1), e.g., cavity 102E. The rinse vessel 200 includes an opening 202 on a bottom surface 204 for receiving a rinse fluid supply line 206 and an opening 208 on a side surface 210 for draining excess rinse fluid. Preferably, the rinse fluid supply line 206 supplies rinsing fluid to the rinse vessel 200 through a known fluid dispersion device 212. The fluid dispersion device 212 disperses the flow of rinse fluid entering the rinse vessel 200 such that, during rinsing, the flow of rinse fluid is not concentrated in any particular area within the rinse vessel 200. By dispersing the flow of rinse fluid, all slides 104 (FIG. 1) positioned within the rinse vessel 200 are subject to substantially the same rinse fluid flow.

Figure 3:
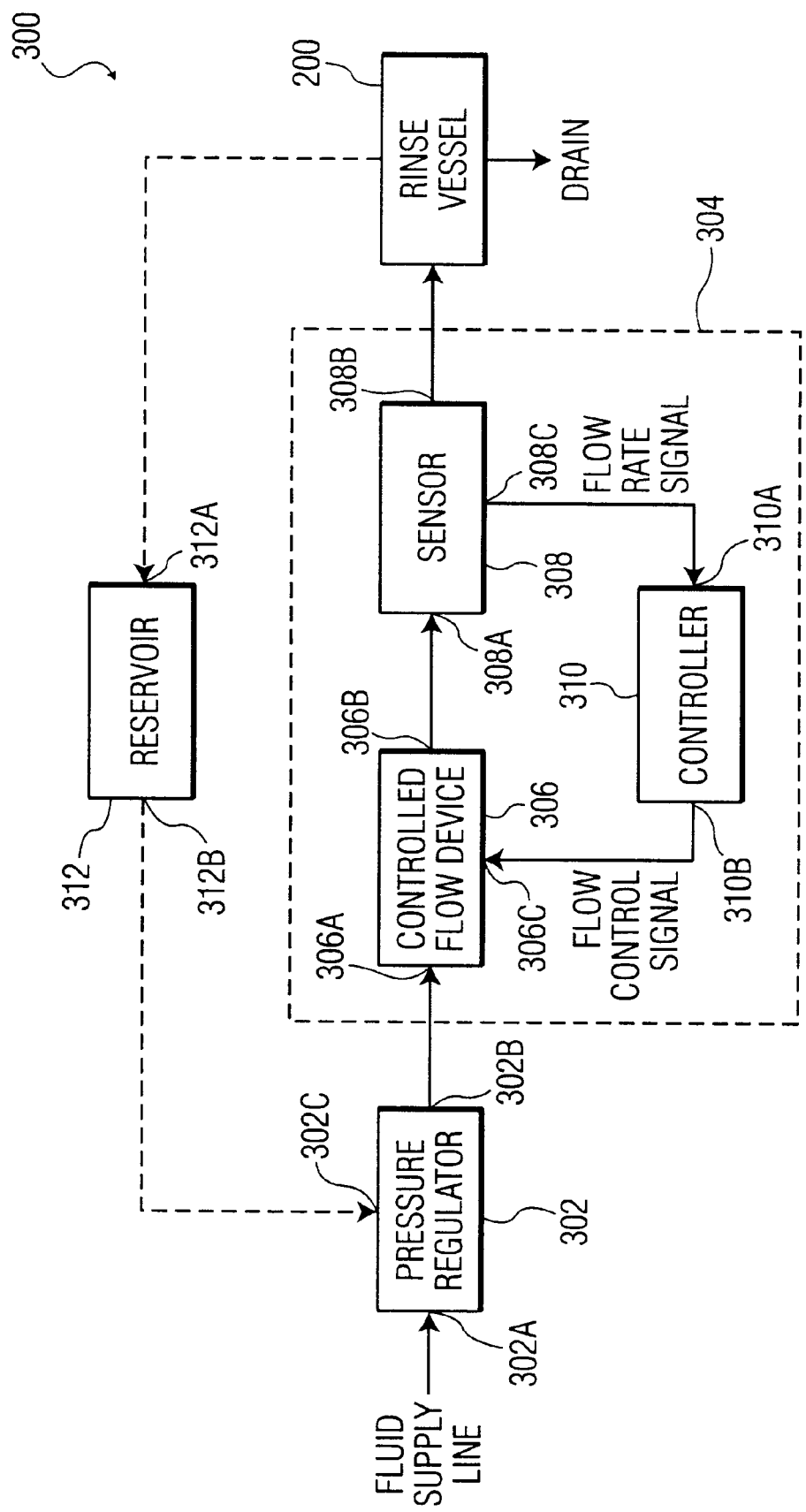
FIG. 3 is a block diagram of a rinse fluid flow control system to supply fluid to the rinse vessel of FIG. 2 for use in the slide stainer of FIG. 1.

FIG. 3 depicts a block diagram of a preferred rinse fluid flow control system 300 for controlling the flow rate of rinse fluid to the rinse vessel 200 of FIG. 2, with the rinse vessel 200 having the same number in both figures. In a general overview, rinse fluid, e.g., water, from a fluid supply line, e.g., a water supply line, passes through a pressure regulator 302 and a flow rate control system 304 to the rinse vessel 200. The pressure regulator 302 limits the pressure of the rinse fluid so that it is compatible with the flow rate control system 304, and the flow rate control system 304 controls the flow rate of the rinse fluid supplied to the rinse vessel 200. The flow rate control system 304 is controlled to deliver to the rinse vessel 200 a specific amount of fluid per unit of time, e.g., a specified number of liters per minute, through the rinse fluid supply line 208 (FIG. 2).

The rinse fluid control system 300 will now be described in detail. The rinse fluid from the fluid supply line enters the pressure regulator 302 through an input port 302A and is passed by the pressure regulator 302 at an output port 302B. In a preferred embodiment, the fluid supply line is a water main supply line, which typically has a pressure of 50–90 PSI in the United States, and the pressure regulator 302 limits the pressure of the rinse fluid at the output port 302B of the pressure regulator 302 to 15 PSI. A suitable pressure regulator for use in the present invention is a Type-860 miniature general purpose regulator available from ControlAir, Inc. of Amherst, N.H., USA.

The illustrated flow rate control system 304 includes a controlled flow device 306, a sensor 308, and a controller 310. In the illustrated embodiment, the controlled flow device 306, the sensor 308, and the controller 310 are connected to form a closed-loop servo control system for monitoring the flow rate of the rinse fluid and maintaining the flow rate at a set rate. Preferably, the flow rate is set to deliver a specified volume or mass per unit of time, e.g., 50 ml/minute.

The regulated rinse fluid from the output port 302B of the pressure regulator 302 enters the controlled flow device 306 through an input port 306A and is passed by the controlled flow device 306 at an output port 306B. A control terminal 306C is used to configure the controlled flow device 306 to control the flow rate of rinse fluid through the controlled flow device 306. The controlled flow device 306 may be a conventional solenoid valve. A suitable controlled flow device 306 for use with the present invention is a proportional solenoid valve Part No. SD8202G67V available from ASCO of Florham Park, N.J., USA.

In the illustrated embodiment, the use of the pressure regulator 302 allows a controlled flow device 306 to be used that is compatible only with low pressures, e.g., pressures less than 20 PSI, which is typically smaller and less expensive than controlled flow devices that are compatible with higher pressures. In alternative embodiments, a controlled flow device 306 is selected that is capable of handling rinse fluid supplied directly by the fluid supply line, thereby rendering the pressure regulator 302 unnecessary. However, depending on the pressure of the rinse fluid from the fluid supply line, this embodiment may require the use of a controlled flow device 306 that is compatible with high pressures, e.g., pressures greater than 50 PSI, which is typically larger and more expensive than controlled flow devices that are compatible with lower pressures.

The flow rate of rinse fluid through the controlled flow device 306 is sensed by the sensor 308. In the illustrated embodiment, the sensor 308 senses the flow rate at the output port 306B of the controlled flow device 306. The sensor 308 has an input port 308A for receiving the controlled rinse fluid from the output port 306B of the controlled flow device 306, an output port 308B for passing the rinse fluid to the rinse vessel 200, and a flow rate terminal 308C for producing a flow rate signal indicating the flow rate of the rinse fluid between the input port 308A and the output port 308B. In a preferred embodiment, the sensor 308 has a negligible effect on the flow rate of the rinse fluid between the output port 306B of the controlled flow device 306B and the rinse vessel 200. Therefore, the flow rate sensed by the sensor 308 provides an indication of the flow rate at the output port 306B of the controlled flow device 306 and the flow rate into the rinse vessel 200. Any effect on flow rate due to the sensor 308 and/or other components between the controlled flow device 306 and the rinse vessel 200 can be accommodated using known techniques. Although, in the illustrated embodiment, the sensor 308 is positioned after the controlled flow device 306, it will be recognized by those skilled in the art that the sensor 308 may be positioned before the controlled flow device 306. A suitable flow sensor for use in the present invention is a FT-110 series TurboFlow® economical flow-rate sensor available from Gems Sensors, Inc. of Plainville, Conn., USA.

The flow rate of the rinse fluid through the controlled flow device 306 is set by the controller 310 based on a predetermined target flow rate and feedback regarding the actual flow rate at the output port 306B of the controlled flow device 306 received from the sensor 308. The predetermined target flow rate may be stored in the controller 310 or supplied to the controller 310 by an operator, e.g., via a keypad 110 (FIG. 1). The controller 310 has a sensor terminal 310A for receiving the flow rate signal from the flow rate terminal 308C of the sensor 308 and a control terminal 310B producing a flow control signal for controlling the controlled flow device 306. The controller 310 generates the flow control signal based on the target flow rate and the actual flow rate indicated by the flow rate signal using known techniques. The controller 310 may be a processor (such as the one described, but not shown, in the discussion of FIG. 1), microprocessor, microcontroller, state machine, logic gates, digital signal processor, analog circuitry, or essentially any device for processing digital and/or analog signals.

In use, the sensor 308 passes a flow rate signal to the controller 310 indicating the flow rate out of the controlled flow device 306. The controller 310 produces a flow control signal based on the flow rate signal to adjust the controlled flow device 306, thereby setting the flow rate at the output port 306B of the controlled flow device 306. If the sensed flow rate out of the controlled flow device 306 is below a target flow rate, the controller 310 adjusts the controlled flow device 306 to increase the flow rate, e.g., by further opening a solenoid valve. On the other hand, if the sensed flow rate is above the target flow rate, the controller 310 adjusts the controlled flow device 306 to lower the flow rate, e.g., by partially closing the solenoid valve. It will be recognized by those skilled in the art that the flow rate control system 304 may employ digital and/or analog components and techniques to set the flow rate.

In one embodiment, the excess rinse fluid from the rinse vessel 200 that exits the rinse vessel 200 through opening 208 (FIG. 2) is passed to a drain for disposal. In an alternative embodiment, the excess fluid from the rinse vessel 200 is collected in a reservoir 312. The reservoir 312 contains a small pump (not shown) that can be used to pump reservoir fluid within the reservoir 312 back to the flow control system 300, where it is reused. In a preferred embodiment, rinse fluid from the reservoir reenters the flow control system through the pressure regulator 302, e.g., through a regulator port 302C. In this manner, the flow control system 300 can be set up to use rinse fluid from a fluid supply line or recycled reservoir fluid from a reservoir 312.

Although the flow control system has been described in terms of a slide stainer such as the one shown in FIG. 1, which is commonly known as a dip and dunk style slide stainer, it is contemplated that the present invention can be used to control the flow of essentially any fluid in any type of slide stainer or other device for processing specimens. For example, it is contemplated that the present invention may be used to control the flow of reagents. In addition, it is contemplated that the flow control system 300 may be used to control the flow of fluids in other known slide stainers such as flood technique slide stainers and spray technique slide stainers. Further, it is contemplated that the flow control system 300 may be used to control the flow of fluids to other devices for processing specimens, e.g., where the specimen is contained within a cup or suspended by a holder, to guard against inadequately stained, rinsed, and/or damaged specimens.

Having thus described a few particular embodiments of the invention, various alterations, modifications, and improvements will readily occur to those skilled in the art. Such alterations, modifications and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A slide stainer with fluid flow control, said slide stainer for rinsing at least one slide using fluid from a fluid supply line, said slide stainer comprising:

a plurality of cavities, a first one of said cavities for applying a first fluid to the at least one slide and a second one of said cavities for rinsing the at least one slide with a second fluid received from the fluid supply line;

a transport for transporting the at least one slide between said first and second cavities; and a flow control system having an input for receiving said second fluid from the fluid supply line and an output coupled to said second cavity, said flow control system sensing the flow rate of said second fluid and adjusting the flow rate to maintain the flow rate of said second fluid to said second cavity at a set rate, said flow control system comprising;

a controlled flow device having an input port for receiving said second fluid from the fluid supply line, an output port for passing said second fluid, and a control terminal for receiving a flow control signal, said controlled flow device controlling the flow rate of said second fluid based on the flow control signal received at the control terminal, wherein said controlled flow device is a proportional solenoid valve;

a sensor coupled to said controlled flow device for sensing the flow rate through said controlled flow device, said sensor having a flow rate terminal producing a flow rate signal indicative of the sensed flow rate; and a controller having a sensor terminal coupled to the flow rate terminal of said sensor and a control terminal coupled to the control terminal of said controlled flow device, said controller producing the flow control signal for controlling said controlled flow device based on the flow rate signal to regulate the flow rate of said second fluid.

2. The slide stainer of claim 1, wherein the set rate is set by an operator.

3. The slide stainer of claim 1, wherein said flow control system is a closed-loop flow control system.

4. The slide stainer of claim 1, further comprising:

a pressure regulator having an input port coupled to the fluid supply line for receiving the second fluid and an output port coupled to the input port of said controlled flow device, said pressure regulator limiting pressure at the output port of the said pressure regulator.

5. The slide stainer of claim 4, further comprising:

a reservoir for receiving excess fluid from said second one of said cavities, said reservoir having an output coupled to said pressure regulator, wherein said pressure regulator supplies said excess fluid to said controlled flow device.

6. The slide stainer of claim 1, wherein the fluid supply line is a water main supply line.

* * * * *